US00PP16326P2

(12) United States Plant Patent
Verheijen

(10) Patent No.: US PP16,326 P2
(45) Date of Patent: Mar. 7, 2006

(54) ***HYPERICUM* PLANT NAMED 'VERIVOCLA'**

(50) Latin Name: *Hypericum androsaemum*
Varietal Denomination: Verivocla

(75) Inventor: Edwin Martijn Verheijen, Wieringerwerf (NL)

(73) Assignee: Handelskwekerij Verheijen vof., Wieringerwerf (NL)

( * ) Notice: Subject to any disclaimer, the term of this patent is extended or adjusted under 35 U.S.C. 154(b) by 4 days.

(21) Appl. No.: 11/046,002

(22) Filed: Jan. 28, 2005

(51) Int. Cl.
*A01H 5/00* (2006.01)

(52) U.S. Cl. ..... Plt./226
(58) Field of Classification Search ..... Plt./226, Plt./263
See application file for complete search history.

*Primary Examiner*—Kent Bell
(74) *Attorney, Agent, or Firm*—C. A. Whealy

(57) ABSTRACT

A new and distinct cultivar of *Hypericum* plant named 'Verivocla', characterized by its upright and outwardly spreading plant habit; dark green leaves; cream-colored fruits; and good postproduction longevity.

2 Drawing Sheets

Botanical designation: *Hypericum androsaemum.*
Cultivar denomination: 'Verivocla'.

BACKGROUND OF THE INVENTION

The present Invention relates to a new and distinct cultivar of *Hypericum* plant, botanically known as *Hypericum androsaemum,* commercially used as cut stems with fruits, and hereinafter referred to by the name 'Verivocla'.

The new *Hypericum* is a product of a planned breeding program conducted by the Inventor in Wieringerwerf, The Netherlands. The objective of the breeding program was to develop cut *Hypericum* varieties with attractive fruit coloration.

The new cultivar originated from a cross-pollination made by the Inventor in January, 2000 of a proprietary selection of *Hypericum* identified as code number 121051, not patented, as the female, or seed, parent with a proprietary selection of *Hypericum* identified as code number 121062, not patented, as the male, or pollen, parent. The cultivar Verivocla was discovered and selected by the Inventor during the summer of 2001 as a flowering plant within the progeny of the stated cross-pollination in a controlled environment in Wieringerwerf, The Netherlands.

Asexual reproduction of the new *Hypericum* by terminal cuttings at Wieringerwerf, The Netherlands since August, 2001, has shown that the unique features of this new *Hypericum* are stable and reproduced true to type in successive generations of asexual reproduction.

SUMMARY OF THE INVENTION

The following traits have been repeatedly observed and are determined to be the unique characteristics of 'Verivocla'. These characteristics in combination distinguish 'Verivocla' as a new and distinct cultivar:

1. Upright and outwardly spreading plant habit.
2. Dark green-colored leaves.
3. Cream-colored fruits.
4. Good postproduction longevity.

Plants of the new *Hypericum* differ from plants of the female parent selection in the following characteristics:

1. Plants of the new *Hypericum* have more compact flower umbels than plants of the female parent selection.
2. Plants of the new *Hypericum* have smaller fruits than plants of the female parent selection.
3. Plants of the new *Hypericum* and the female parent selection differ in fruit coloration as plants of the female parent selection have darker cream-colored fruits.

Plants of the new *Hypericum* differ from plants of the male parent selection in the following characteristics:

1. Plants of the new *Hypericum* have longer stems than plants of the male parent selection.
2. Plants of the new *Hypericum* have more rounded fruits than plants of the male parent selection.
3. Plants of the new *Hypericum* and the male parent selection differ in fruit coloration as plants of the male parent selection have brownish white-colored fruits.

Plants of the new *Hypericum* can be compared to plants of the *Hypericum* cultivar Excellent Flair, not patented. In side-by-side comparisons conducted in Wieringerwerf, The Netherlands, plants of the new *Hypericum* differed from plants of the cultivar Excellent Flair in the following characteristics:

1. Plants of the new *Hypericum* had shorter and darker green-colored leaves than plants of the cultivar Excellent Flair.
2. Leaves of plants of the new *Hypericum* did not scorch as a symptom of low leaf magnesium whereas leaves of plants of the cultivar Excellent Flair scorched.
3. Plants of the new *Hypericum* had smaller inflorescences with fewer flowers per inflorescence than plants of the cultivar Excellent Flair.
4. Plants of the new *Hypericum* produced slightly smaller fruits than plants of the cultivar Excellent Flair.
5. Fruits of plants of the new *Hypericum* were cream in color whereas fruits of plants of the cultivar Excellent Flair were brownish red in color.

BRIEF DESCRIPTION OF THE PHOTOGRAPHS

The accompanying colored photographs illustrate the overall appearance of the new *Hypericum*, showing the colors as true as it is reasonably possible to obtain in colored reproductions of this type. Colors in the photographs may differ slightly from the color values cited in the detailed botanical description which accurately describe the colors of the new *Hypericum*.

The photograph on the first sheet comprises a side perspective view of a typical flowering stem of 'Verivocla'.

The photograph at the top of the second sheet is a close-up view of typical fruits of 'Verivocla'.

The photograph at the bottom of the second sheet is a close-up view of a typical flower and developing fruits of 'Verivocla'.

DETAILED BOTANICAL DESCRIPTION

The new *Hypericum* has not been observed under all possible environmental conditions. The phenotype may vary somewhat with variations in environment such as temperature and light intensity, without, however, any variance in genotype.

The aforementioned photographs, following observations and measurements describe plants grown in Wieringerwerf, The Netherlands, in an outdoor nursey and under commercial production practices. Plants used for the photographs and the description were about two years old. The photographs and description were taken during the summer with day temperatures ranging from 14 to 30° C. and night temperatures ranging from 7 to 14° C. In the following description, color references are made to The Royal Horticultural Society Colour Chart, 2001 Edition, except where general terms of ordinary dictionary siginficance are used.

Botanical classification: *Hypericum androsaemum* cultivar Verivocla.

Parentage:

*Female parent.*—Proprietary selection of *Hypericum androsaemum* identified as code number 121051, not patented.

*Male parent.*—Proprietary selection of *Hypericum androsaemum* identified as code number 121062, not patented.

Propagation:

*Type.*—Terminal cuttings.

*Time to initiate roots, summer.*—About two weeks at 20° C.

*Time to initiate roots, winter.*—About three weeks at 20° C.

*Time to produce a rooted cutting, summer.*—About 30 days at 20° C.

*Time to produce a rooted cutting, winter.*—About 40 days at 20° C.

*Root description.*—Fine, fibrous grayed orange, 163C overlain with 200B, in color.

*Rooting habit.*—Freely branching; dense.

Plant description:

*Plant form.*—Upright and outwardly spreading perennial woody shrub.

*Growth habit.*—Moderately vigorous. Freely basal branching; dense and bushy growth habit.

*Plant height.*—About 70 cm.

*Plant width* (*spread*).—About 60 cm.

*Quantity of stems per year.*—About 10.

*Lateral branches.*—Length: About 20 cm. Diameter: About 2.2 mm. Internode length: About 4.5 cm. Strength: Moderate. Texture: Smooth, glabrous. Color, young: 145C. Color, mature: 145C overlain with 165A.

*Foliage description.*—Arrangement: Opposite; simple; sessile. Length: About 7 cm. Width: About 4 cm. Shape: Ovate. Apex: Retuse. Base: Obtuse to cordate. Margin: Entire; slightly undulate. Texture, upper surface: Glabrous; slightly rugose. Texture, lower surface: Glabrous; rugose. Venation pattern: Pinnate. Color: Developing leaves, upper surface: 143A. Developing leaves, lower surface: 193A. Fully expanded leaves, upper surface: Darker than 139A; venation, 145B. Fully expanded leaves, lower surface: 194B; venation, 145C. Stipule length: About 8 mm. Stipule diameter: About 4 mm. Stipule texture, upper and lower surfaces: Smooth, glabrous. Color, upper surface: 139A. Color, lower surface: 194C.

Flower description:

*Flower type and habit.*—Bright yellow single flowers arranged in terminal compound umbels with about eleven flowers per umbel. Flowers not fragrant. Flowers persistent. Flowers face mostly upright to slightly outwardly.

*Natural flowering season.*—Summer, typically June to September in The Netherlands.

*Postproduction longevity.*—Cut flower are typically harvested when all flowers have delevoped fruits. Postproduction longevity of cut stems with fruits in about two weeks.

*Inflorescence height.*—About 5 cm.

*Inflorescence diameter.*—About 6 cm.

*Flower buds.*—Height: About 1.1 cm. Diameter: About 7.5 mm. Shape: Elliptic. Color: 13B; longitudinal stripes, 163B.

*Flowers.*—Diameter: About 2.8 cm. Depth: About 1.1 cm.

*Petals.*—Quantity per flower: Five. Length: About 1.3 cm. Width: About 7 mm. Shape: Broadly elliptic. Apex: Acute. Base: Attenuate. Margin: Entire. Aspect: Concave. Texture, upper and lower surfaces: Smooth; glabrous. Color: Developing and fully expanded petals, upper surface: 14B; color does not fade with development. Developing and fully expanded petals, lower surface: 13C.

*Sepals.*—Quantity per flower: Five. Length: About 8 mm. Width: About 7 mm. Shape: Elliptic. Apex: Acute to obtuse. Base: Broadly cuneate. Margin: Entire. Texture, upper surface: Smooth; glabrous. Texture, lower surface: Slightly rugose; glabrous. Color: Developing sepals, upper surface: 144A. Developing sepals, lower surface: 145D to 141C. Fully expanded sepals, upper surface: 137B to 144B. Fully expanded sepals, lower surface: 192A to 192B.

*Peduncles.*—Length: About 1.4 cm. Diameter: About 1.5 mm. Orientation: Erect to about 45° from vertical. Strength: Moderately strong. Texture: Smooth, glabrous. Color: 143A.

*Pedicels.*—Length: About 1 cm. Diameter: About 1.5 mm. Orientation: Erect to about 45° from vertical. Strength: Moderately strong. Texture: Smooth, glabrous. Color: 144B.

*Reproductive organs.*—Stamens: Quantity per flower: About 75. Filament color: 9C. Anther shape: Globular. Anther length: About 1 mm. Anther color: 21A. Pollen amount: Moderate. Pollen color: 12C. Pistils: Quantity per flower: Three. Pistil length: About 8 mm. Stigma shape: Globular. Stigma color: 186A.

Style length: About 4 mm. Style color: 154C. Ovary color: 151D.

*Fruits.*—Quantity per flower: One. Days to ripening: About 25. Type: Capsule. Shape: Ellipsoidal. Length: About 1.2 cm. Diameter: About 1 cm. Texture: Smooth; glabrous. Color: 4D; towards the apex, 163A.

*Seeds.*—Quantity per flower: More than 100. Length: About 1 mm. Diameter: About 0.5 mm. Texture: Smooth; glabrous. Color: 165A.

Disease/pest resistance: Plants of the new *Hypericum* have been observed to be resistant to Rust. Plants of the new *Hypericum* have not been observed to be resistant to pests and other pathogens common to *Hypericum* .

Temperature tolerance: Plants of the new *Hypericum* have been observed to tolerate temperatures ranging from −15 to 35° C.

It is claimed:

1. A new and distinct cultivar of *Hypericum* plant named 'Verivocla', as illustrated and described.

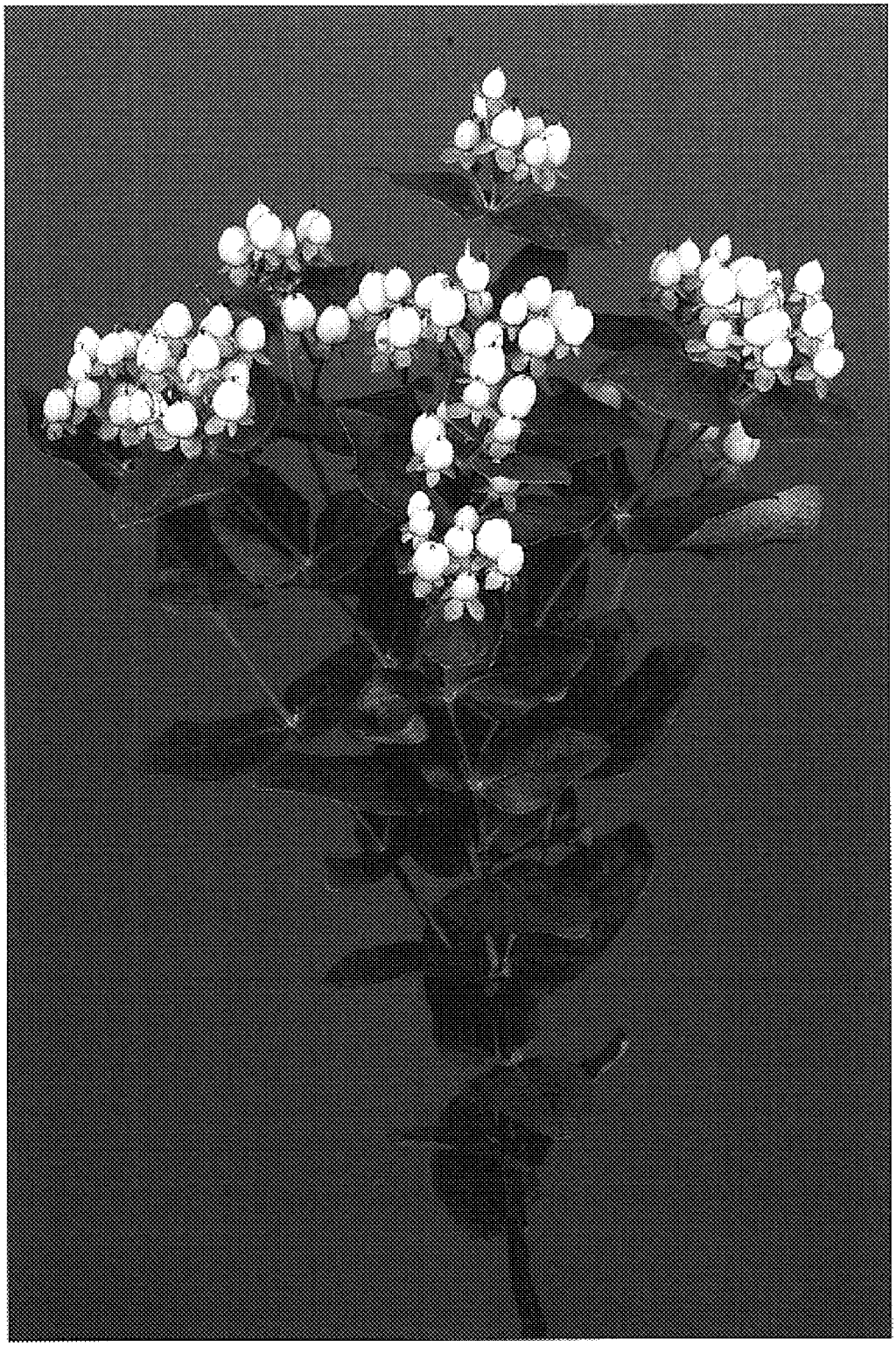

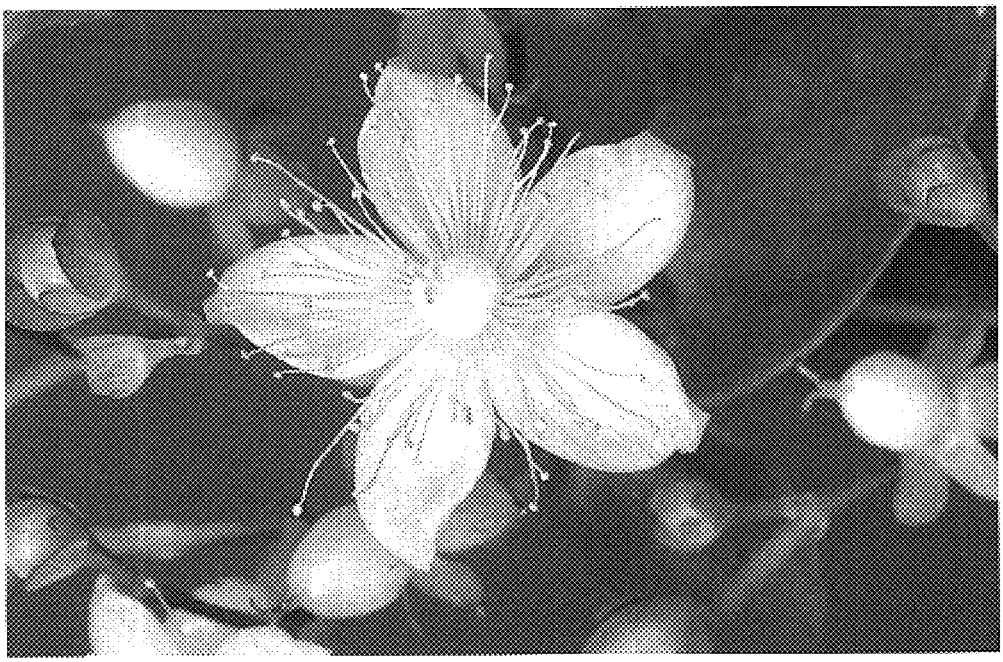
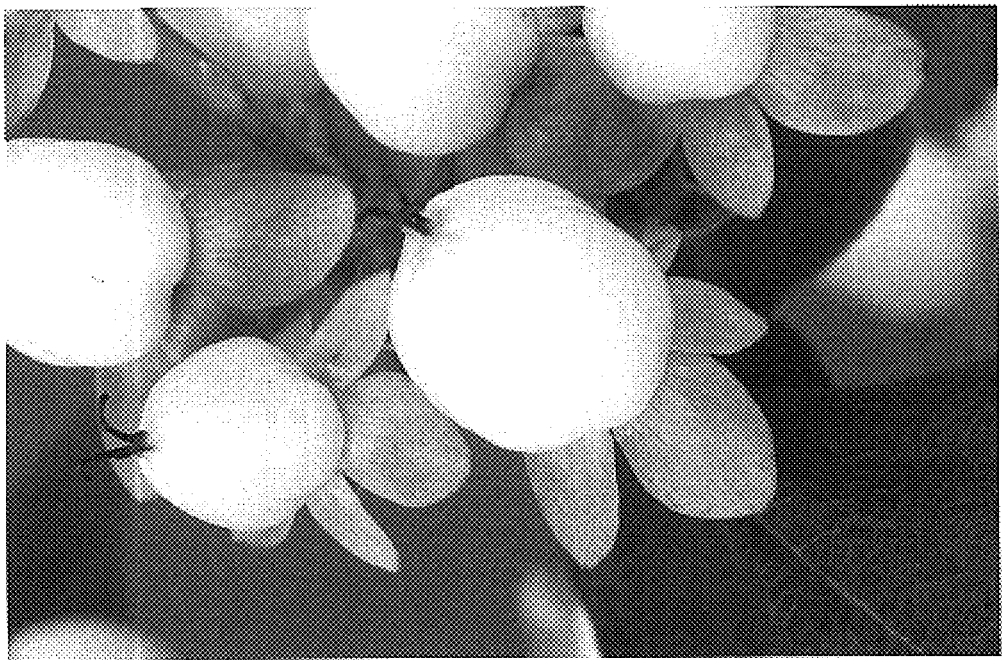

* * * * *